(12) United States Patent
Liu et al.

(10) Patent No.: US 11,733,141 B1
(45) Date of Patent: Aug. 22, 2023

(54) SYSTEM AND METHOD FOR DETERMINING ROCK WETTABILITY BASED ON CONTACT ANGLE MEASUREMENT AND CORRECTION OF MULTIPLE OIL GLOBULES

(71) Applicant: INSTITUTE OF GEOLOGY AND GEOPHYSICS, CHINESE ACADEMY OF SCIENCES, Beijing (CN)

(72) Inventors: Naigui Liu, Beijing (CN); Likuan Zhang, Beijing (CN); Zhijun Jin, Beijing (CN); Hansheng Ji, Beijing (CN); Jianzhao Yan, Beijing (CN); Wang Zhang, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 18/131,911

(22) Filed: Apr. 7, 2023

(30) Foreign Application Priority Data

Apr. 7, 2022 (CN) .......................... 202210359694.2

(51) Int. Cl.
*G01N 13/02* (2006.01)
*G01N 33/24* (2006.01)
(52) U.S. Cl.
CPC ............. *G01N 13/02* (2013.01); *G01N 33/24* (2013.01); *G01N 2013/0208* (2013.01)

(58) Field of Classification Search
CPC ........ G01N 13/00; G01N 13/02; G01N 33/24; G01N 2013/0208
See application file for complete search history.

(56) References Cited

U.S. PATENT DOCUMENTS 10,226,202 B2 * 3/2019 Takeshita ................. G06T 7/20
2019/0242804 A1 8/2019 Alshehri et al.

FOREIGN PATENT DOCUMENTS

| CN | 202854008 U | 4/2013 |
| CN | 105939779 A | 9/2016 |
| CN | 108593501 A | 9/2018 |
| CN | 109991130 A | 7/2019 |
| CN | 111855502 A | 10/2020 |

(Continued)

*Primary Examiner* — Nguyen Q. Ha
(74) *Attorney, Agent, or Firm* — Bayramoglu Law Offices LLC

(57) ABSTRACT

A method for determining rock wettability based on contact angle measurement and correction of multiple oil globules includes: saturating a rock sample with oil, placing a shooting angle calibration circle on a measurement surface of the rock sample, and placing the rock sample saturated with oil in water for water imbibition and oil displacement to form a rock sample with multiple oil globules; acquiring an image of a measurement surface of the rock sample with multiple oil globules at a shooting angle α and a deformation degree of the calibration circle in a shooting field of view, and calculating the shooting angle α; correcting, based on the shooting angle α, a contact angle measurement value γ through a contact angle correction model to acquire a contact angle correction value θ; and determining, based on the contact angle correction value θ, wettability of the rock sample.

10 Claims, 6 Drawing Sheets

(56) References Cited

FOREIGN PATENT DOCUMENTS

| CN | 112557259 | A | 3/2021 | | |
|---|---|---|---|---|---|
| CN | 113049453 | A | 6/2021 | | |
| CN | 113390759 | A | 9/2021 | | |
| RU | 2744463 | C1 | 3/2021 | | |
| WO | WO-2014029191 | A1 * | 2/2014 | ............. | G01N 13/02 |

* cited by examiner

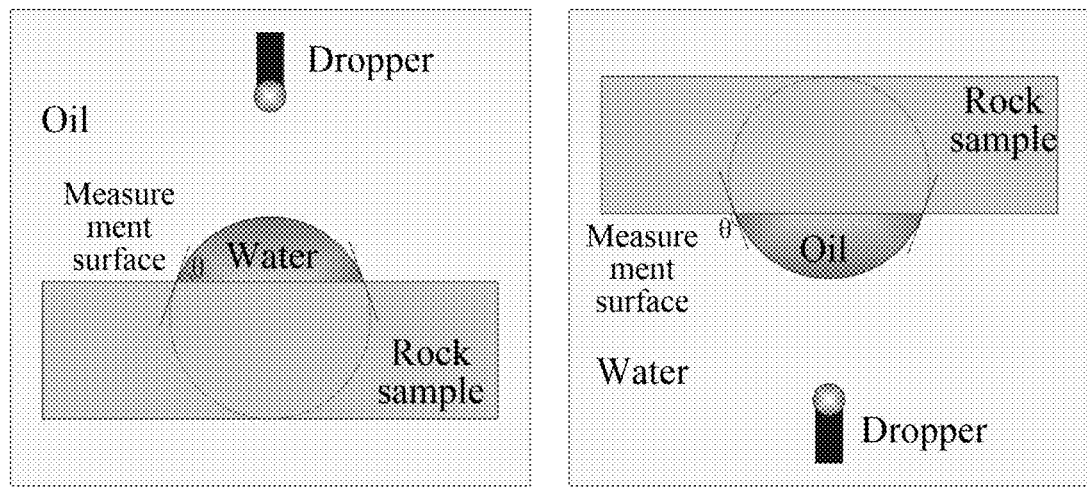

FIG. 1(Prior Art)

```
┌─────────────────────────────────────────────────────────┐
│ Saturate a rock sample with oil, place a shooting angle │
│ calibration circle on a measurement surface of the rock │
│ sample, and place the rock sample saturated with oil in │
│ water for a set time to form a rock sample with         │
│ multiple oil globules                                   │
└─────────────────────────────────────────────────────────┘
                            │
                            ▼
┌─────────────────────────────────────────────────────────┐
│ Acquire an image of the measurement surface of the rock │
│ sample with multiple oil globules at any shooting angle │
│ and a deformation degree of the calibration circle in a │
│ shooting field of view, and calculate the shooting angle│
└─────────────────────────────────────────────────────────┘
                            │
                            ▼
┌─────────────────────────────────────────────────────────┐
│ Correct, based on the shooting angle, a contact angle   │
│ measurement value through a contact angle correction    │
│ model to acquire a contact angle correction value       │
└─────────────────────────────────────────────────────────┘
                            │
                            ▼
┌─────────────────────────────────────────────────────────┐
│ Determine, based on the contact angle correction value, │
│ wettability of the rock sample                          │
└─────────────────────────────────────────────────────────┘
```

FIG. 2

SYSTEM AND METHOD FOR DETERMINING ROCK WETTABILITY BASED ON CONTACT ANGLE MEASUREMENT AND CORRECTION OF MULTIPLE OIL GLOBULES

CROSS REFERENCE TO THE RELATED APPLICATIONS

This application is based upon and claims priority to Chinese Patent Application No. 202210359694.2, filed on Apr. 7, 2022, the entire contents of which are incorporated herein by reference.

TECHNICAL FIELD

The present disclosure belongs to the field of rock wettability measurement and specifically relates to a system and method for determining rock wettability based on contact angle measurement and correction of multiple oil globules.

BACKGROUND

Wettability describes a preference of one fluid over another to wet (spread over or adhere to) a solid surface when there are two or more immiscible fluids on the solid surface. In petroleum geology, wettability can be divided into water wettability (hydrophilicity) and oil wettability (lipophilicity) on a macro level according to the oil-water-rock surface interaction. For example, in oil-water-coexisting pores, if water is more easily adhered to the rock, then water is a wetting phase, oil is a non-wetting phase, and the rock is hydrophilic. On the contrary, oil is a wetting phase, water is a non-wetting phase, and the rock is lipophilic.

The surface properties of different rock mineral grains vary greatly. Moreover, oil and gas have made different alterations to rock wettability during geological history, resulting in a strong heterogeneity in rock wettability, which is referred to as mixed wettability.

Contact angle is an angle formed between the liquid/gas interface and the solid surface, and is a system of three different interfaces interacting with each other. In the field of petroleum geology and experiments, the contact angle method is the main method for characterizing the wettability of reservoir rocks. The three-phase interfaces generally refer to the interfaces between oil, water, and rock. FIG. 1 is a schematic diagram showing contact angle measurement in the prior art. In the measurement, a rock sample is placed at the bottom of an oil container or the top of a water container, and water/oil is dropped onto the upper or lower surface of the rock sample through a dropper, meanwhile obtaining images from an angle parallel to the measurement surface of the rock sample, so as to measure the contact angle $\theta$. The contact angle $\theta$ is an angle between the water phase and the rock surface or a supplementary angle of an angle between the oil phase and the rock surface (in this case, to reduce the impact of buoyancy, only droplets with a diameter of less than 2 mm are measured). The contact angle method is intuitive and convenient. However, it adopts single-point measurement, which has poor representativeness, and due to insufficient oil-water-rock contact, the measurement results is inaccurate.

SUMMARY

In order to solve the above problem in the prior art, that is, the contact angle method in the prior art adopts single-point measurement, which has poor representativeness and cannot comprehensively describe rock wettability, a first aspect of the present disclosure provides a system for determining rock wettability based on contact angle measurement and correction of multiple oil globules. The system includes a first treatment tank, a second treatment tank, a mechanical arm, an image acquisition device, and a control processor, where The first treatment tank is an oil tank and the second treatment tank is a water tank. The oil tank and the water tank are arranged in an operation zone of the mechanical arm.

The mechanical arm is configured to receive a first control signal and a second control signal from the control processor.

The mechanical arm is further configured to grab a target rock sample based on the first control signal, place the target rock sample in the first treatment tank, and maintain a set first time to saturate the target rock sample with oil.

The mechanical arm is further configured to place the target rock sample saturated with oil in the second treatment tank based on the second control signal and maintain a set second time for water imbibition and oil displacement, such that multiple oil globules appear on a measurement surface of the target rock sample to form a rock sample with multiple oil globules, where a measurement surface of the rock sample with multiple oil globules is provided with a shooting angle calibration circle.

The image acquisition device is configured to receive an image acquisition control signal from the control processor and photograph the measurement surface of the rock sample with multiple oil globules at any shooting angle $\alpha$.

The control processor is configured to generate the first control signal, the second control signal, and the image acquisition control signal, and control the mechanical arm and the image acquisition device separately. The control processor is further configured to determine, based on an image of the measurement surface of the rock sample with multiple oil globules acquired by the image acquisition device at any shooting angle $\alpha$, wettability of the rock sample by a method for determining rock wettability based on contact angle measurement and correction of multiple oil globules.

A second aspect of the present disclosure proposes the method for determining rock wettability based on contact angle measurement and correction of multiple oil globules, which is based on the system for determining rock wettability based on contact angle measurement and correction of multiple oil globules, and includes:

S10: saturating the rock sample with oil, placing the shooting angle calibration circle on the measurement surface of the rock sample, and placing the rock sample saturated with oil in water for a set time to form the rock sample with multiple oil globules;

S20: acquiring the image of the measurement surface of the rock sample with multiple oil globules at any shooting angle $\alpha$ and a deformation degree of the calibration circle in a shooting field of view, and calculating the shooting angle $\alpha$;

S30: correcting, based on the shooting angle $\alpha$, a contact angle measurement value $\gamma$ through a contact angle correction model to acquire a contact angle correction value $\theta$; and S40: determining, based on the contact angle correction value $\theta$, the wettability of the rock sample.

In some preferred embodiments, the shooting angle $\alpha$ is expressed as:

$$\alpha = \arcsin\left(\frac{S}{L}\right)$$

where, S denotes a length of a minor axis of a deformed ellipse of the calibration circle in the shooting field of view, L denotes a length of a major axis of the deformed ellipse of the calibration circle in the shooting field of view, and arcsin denotes an arcsine function.

In some preferred embodiments, the contact angle correction model is built as follows:

A10: setting a current shooting angle as a and building, by taking any oil globule as a part of a sphere for sphere fitting, a physical model of the oil globule and the measurement surface of the rock sample based on an interfacial tension;

A20: setting a contact surface between the oil globule and the measurement surface of the rock sample in the physical model as a plane BKCL; setting a center of a circle formed by the plane BKCL as a point J; setting a shooting plane as a plane GKHL; setting a center of a circle formed by the plane GKHL as a point I and a radius of the circle as r; setting a center of a fitted sphere as a point O and a radius of the fitted sphere as R; setting a distance between the point I and the point J as a line segment IJ, a distance between the point O and the point J as a line segment OJ, and a distance between the point O and the point I as a line segment OI; setting a supplementary angle of the contact angle measurement value γ as an angle β and a supplementary angle of the contact angle correction value θ as an angle φ; and deriving a mapping relation between the distance and the angle in the physical model based on a side-angle relation of a right triangle;

where, the mapping relation between the distance and the angle in the physical model includes: a mapping relation from the line segment IJ to the radius r and the angle β; a mapping relation from the line segment IJ to the line segment OJ and the shooting angle α; a mapping relation from the line segment OJ to the radius R and the angle φ; a mapping relation from the line segment OI to the line segment OJ and the shooting angle α; a triangle relation of the radius R, the radius r, and the line segment OI; a supplementary relation between the angle β and the contact angle measurement value γ; and a supplementary relation between the angle φ and the contact angle correction value θ; and A30: converting and solving the mapping relation between the distance and the angle in the physical model to acquire a mapping relation from the contact angle correction value θ to the shooting angle α and the contact angle measurement value γ as the contact angle correction model.

In some preferred embodiments, the mapping relation from the line segment IJ to the radius r and the angle β is expressed as follows:

$$IJ = r \cos \beta$$

where, cos denotes a cosine function.

In some preferred embodiments, the mapping relation from the line segment IJ to the line segment OJ and the shooting angle α is expressed as follows:

$$IJ = OJ \cos \alpha$$

where, cos denotes a cosine function.

In some preferred embodiments, the mapping relation from the line segment OJ to the radius R and the angle φ is expressed as follows:

$$OJ = R \cos \varphi$$

where, cos denotes a cosine function.

In some preferred embodiments, the mapping relation from the line segment OI to the line segment OJ and the shooting angle α is expressed as follows:

$$OI = OJ \sin \alpha$$

where, sin denotes a sine function.

In some preferred embodiments, the triangle relation of the radius R, the radius r, and the line segment OI, the supplementary relation between the angle β and the contact angle measurement value γ, and the supplementary relation between the angle φ and the contact angle correction value θ are expressed as follows:

$$OI^2 + r^2 = R^2$$

$$\gamma = 180 - \beta$$

$$\theta = 180 - \varphi$$

In some preferred embodiments, the contact angle correction value θ is expressed as:

$$\theta = \arccos\left(\frac{\cos \gamma}{\sqrt{\sin^2 \alpha \cos^2 \gamma + \cos^2 \alpha}}\right)$$

where, arccos denotes an arccosine function, cos denotes a cosine function, and sin denotes a sine function.

A third aspect of the present disclosure provides a system for determining rock wettability based on contact angle measurement and correction of multiple oil globules, which includes the following modules:

a rock sample preparation module configured to saturate a rock sample with oil, place a shooting angle calibration circle on a measurement surface of the rock sample, and place the rock sample saturated with oil in water for a set time to form a rock sample with multiple oil globules;

a shooting angle acquisition module configured to acquire an image of the measurement surface of the rock sample with multiple oil globules at any shooting angle α and a deformation degree of the calibration circle in a shooting field of view, and calculate the shooting angle α;

a contact angle correction module configured to correct, based on the shooting angle α, a contact angle measurement value γ through a contact angle correction model to acquire a contact angle correction value θ; and a wettability determination module configured to determine, based on the contact angle correction value θ, the wettability of the rock sample.

The present disclosure has the following beneficial effects:

(1) In the present disclosure, the rock sample is completely saturated with oil and placed in water. Through water imbibition and oil displacement, multiple oil globules appear on the measurement surface of the rock sample. In order to prevent the multiple oil globules from blocking each other, a camera is placed at a certain angle with the measurement surface, thereby acquiring an image of the spontaneous water imbibition and oil displacement of the rock sample. The oil-water-rock contact angle measurement value of the measurement surface is calculated and corrected based on the image. The present disclosure adopts multi-point synchronous measurement, which has strong representativeness and can characterize the mixed wettability of the rock sample. In addition, in the present disclosure, the oil globule can fully contact water and the rock surface, making the characterization of wettability more accurate.

(2) The present disclosure deduces the relation of the contact angle correction value, the contact angle measurement value and the shooting angle, acquires errors corresponding to different contact angle measurement values, and acquires the contact angle correction value, further improving the accuracy of the final result.

(3) The present disclosure provides an error chart of contact angle measurement values and contact angle correction values at different shooting angles. In practical operation, the contact angle measurement value and shooting angle of a certain oil globule are first determined, and then the error corresponding to the contact angle measurement value on the corresponding shooting angle curve is selected according to the error chart. In this way, the error chart can visually compare the error change between the contact angle measurement value γ and the contact angle correction value θ at different shooting angles.

BRIEF DESCRIPTION OF THE DRAWINGS

Other features, objectives and advantages of the present disclosure will become more apparent upon reading the detailed description of the non-restrictive embodiments with reference to the following drawings.

FIG. 1 is a schematic diagram of contact angle measurement in the prior art.

FIG. 2 is a flowchart of a method for determining rock wettability based on contact angle measurement and correction of multiple oil globules according to the present disclosure.

DETAILED DESCRIPTION OF THE EMBODIMENTS

Figure 3:
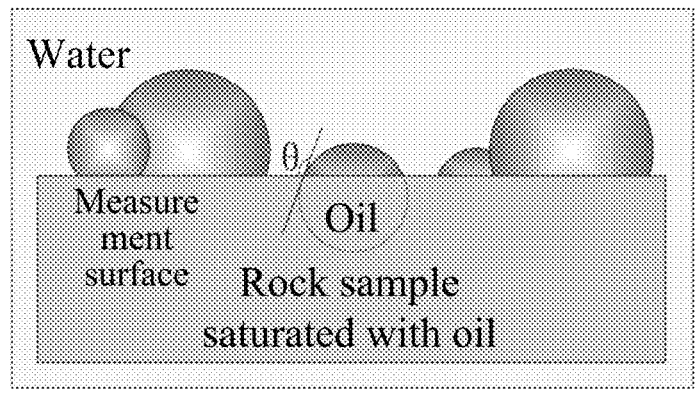
FIG. 3 is a schematic diagram of contact angle measurement of a rock sample in an embodiment of the method for determining rock wettability based on contact angle measurement and correction of multiple oil globules according to the present disclosure.

The present disclosure will be further described in detail below in conjunction with the drawings and embodiments. It should be understood that the specific embodiments described herein are merely intended to explain the present disclosure, rather than to limit the present disclosure. It should also be noted that, for convenience of description, only the parts related to the present disclosure are shown in the drawings.

It should be noted that the examples in the disclosure and features in the examples may be combined with each other in a non-conflicting situation. The present disclosure will be described in detail below with reference to the drawings and embodiments.

A first embodiment of the present disclosure provides a system for determining rock wettability based on contact angle measurement and correction of multiple oil globules. The system includes a first treatment tank, a second treatment tank, a mechanical arm, an image acquisition device, and a control processor.

The first treatment tank is an oil tank and the second treatment tank is a water tank and the oil tank and the water tank are arranged in an operation zone of the mechanical arm.

The mechanical arm is configured to receive a first control signal and a second control signal from the control processor.

The mechanical arm is further configured to grab a target rock sample based on the first control signal, place the target rock sample in the first treatment tank, and maintain a set first time to saturate the target rock sample with oil.

The mechanical arm is further configured to place the target rock sample saturated with oil in the second treatment tank based on the second control signal, and maintain a set second time for water imbibition and oil displacement, such that multiple oil globules appear on a measurement surface of the target rock sample to form a rock sample with multiple oil globules, where a measurement surface of the rock sample with multiple oil globules is provided with a shooting angle calibration circle.

The image acquisition device is configured to receive an image acquisition control signal from the control processor and photograph the measurement surface of the rock sample with multiple oil globules at any shooting angle α.

The control processor is configured to generate the first control signal, the second control signal, and the image acquisition control signal, and control the mechanical arm and the image acquisition device separately; and the control processor is further configured to determine, based on an image of the measurement surface of the rock sample with multiple oil globules acquired by the image acquisition device at any shooting angle α, wettability of the rock sample by a method for determining rock wettability based on contact angle measurement and correction of multiple oil globules.

In order to more clearly describe the system and method for determining rock wettability based on contact angle measurement and correction of multiple oil globules provided by the present disclosure, the embodiments of the present disclosure are described in detail below with reference to the drawings of the present disclosure.

In a first embodiment of the present disclosure, the system for determining rock wettability based on contact angle measurement and correction of multiple oil globules includes a first treatment tank, a second treatment tank, a mechanical arm, an image acquisition device, and a control processor.

The first treatment tank is an oil tank and the second treatment tank is a water tank and the oil tank and the water tank are arranged in an operation zone of the mechanical arm.

The mechanical arm is configured to receive a first control signal and a second control signal from the control processor.

The mechanical arm is further configured to grab a target rock sample based on the first control signal, place the target rock sample in the first treatment tank, and maintain a set first time to saturate the target rock sample with oil.

The mechanical arm is further configured to place the target rock sample saturated with oil in the second treatment tank based on the second control signal, and maintain a set second time for water imbibition and oil displacement, such that multiple oil globules appear on a measurement surface of the target rock sample to form a rock sample with multiple oil globules, where a measurement surface of the rock sample with multiple oil globules is provided with a shooting angle calibration circle.

The image acquisition device is configured to receive an image acquisition control signal from the control processor and photograph the measurement surface of the rock sample with multiple oil globules at any shooting angle α.

The control processor is configured to generate the first control signal, the second control signal, and the image acquisition control signal, and control the mechanical arm and the image acquisition device separately; and the control processor is further configured to determine, based on an image of the measurement surface of the rock sample with multiple oil globules acquired by the image acquisition device at any shooting angle α, wettability of the rock sample by a method for determining rock wettability based on contact angle measurement and correction of multiple oil globules.

A second embodiment of the present disclosure proposes the method for determining rock wettability based on contact angle measurement and correction of multiple oil globules, which is based on the system for determining rock wettability based on contact angle measurement and correction of multiple oil globules, and includes steps S10 to S40. As shown in FIG. 2, these steps are as follows:

S10: the rock sample is saturated with oil, the shooting angle calibration circle is placed on the measurement surface of the rock sample, and the rock sample saturated with oil is placed in water for a set time to form the rock sample with multiple oil globules.

FIG. 3 is a schematic diagram of a contact angle measurement of a rock sample in an embodiment of the method for determining rock wettability based on contact angle measurement and correction of multiple oil globules according to the present disclosure. In the measurement, the rock sample is completely saturated with oil and placed in water.

Through water imbibition and oil displacement, multiple oil globules appear on the measurement surface of the rock sample. The image is taken from an angle at which the camera is slightly higher than the measurement surface of the rock sample, and the contact angle distribution is calculated. The contact angle is a supplementary angle of the angle between the oil phase and the rock surface. To reduce the impact of buoyancy, only globules with a diameter of less than 2 mm are measured. In practical applications, if there is too little oil imbibed, an external force can be applied to make more oil globules appear on the measurement surface of the rock sample. The specific process will not be described in detail herein.

Figure 4:
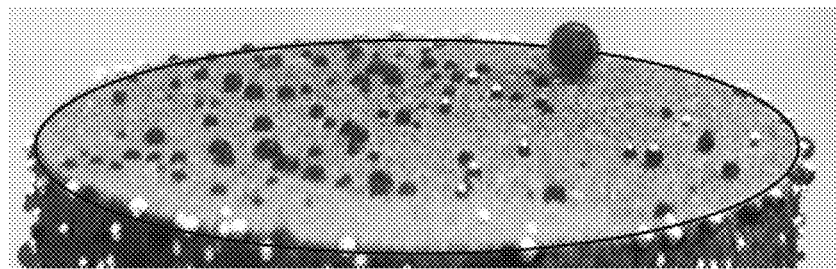
FIG. 4 is a schematic diagram of spontaneous water imbibition and oil displacement on a rock sample in an embodiment of the method for determining rock wettability based on contact angle measurement and correction of multiple oil globules according to the present disclosure.
Figure 5:
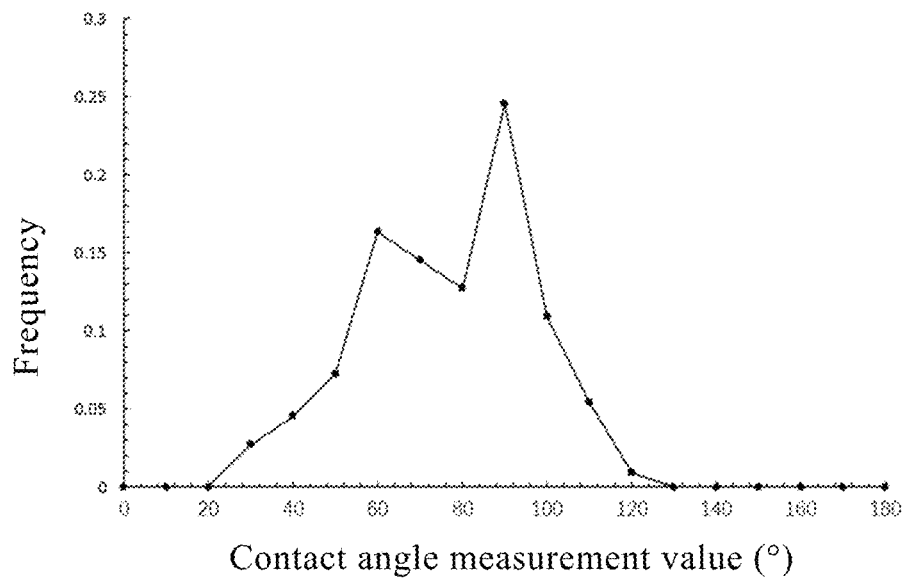
FIG. 5 is a frequency map of contact angle measurement values in an embodiment of the method for determining rock wettability based on contact angle measurement and correction of multiple oil globules according to the present disclosure.

FIG. 4 is a schematic diagram of spontaneous water imbibition and oil displacement of a rock sample in an embodiment of the method for determining rock wettability based on contact angle measurement and correction of multiple oil globules according to the present disclosure. The rock sample is cylindrical, with a porosity of 14.22%, a permeability of 0.2 mD, a diameter of 25 mm, and a length of 42 mm. It can be seen from the figure that a large number of oil globules appear on the measurement surface (upper surface) and periphery of the rock sample. The present disclosure only measures the contact angle of oil globules with a diameter of less than 2 mm on the upper surface, so as to acquire the contact angle measurement value and calculate the contact angle distribution. The present disclosure ignores oil globules located on the side of the rock sample and those with a diameter of greater than 2 mm. Sometimes, in order to photograph more oil globules clearly, images are taken from different directions and angles. To capture oil globules of appropriate size, images can be taken at different times. FIG. 5 is a frequency map of contact angle measurement values in an embodiment of the method for determining rock wettability based on contact angle measurement and correction of multiple oil globules according to the present disclosure. This frequency map shows the measurement and calculation results of the spontaneous water imbibition and oil displacement of the rock sample shown in FIG. 4. In this embodiment, the mutual shielding of oil globules on the measurement surface of the rock sample is not serious, so only the results of spontaneous imbibition of the rock sample for 24 hours at one shooting angle are counted. If it is necessary to analyze the results at multiple shooting angles, the contact angle measurement values should be separately counted for later correction. The specific counting process will not be described in detail herein.

The imbibition contact angle measurement method can be used to calculate the wetting angles of multiple points on the surface of the rock sample, which can better reflect the mixed wettability of the rock sample than the conventional contact angle measurement method. The oil globules can fully contact with water and the rock surface, making the characterization of wettability more accurate. Due to the shooting angle, there is a certain experimental error in the contact angle measurement value, which requires correction to acquire the contact angle correction value, so as to more truly reflect the wettability of the rock sample.

Figure 6:
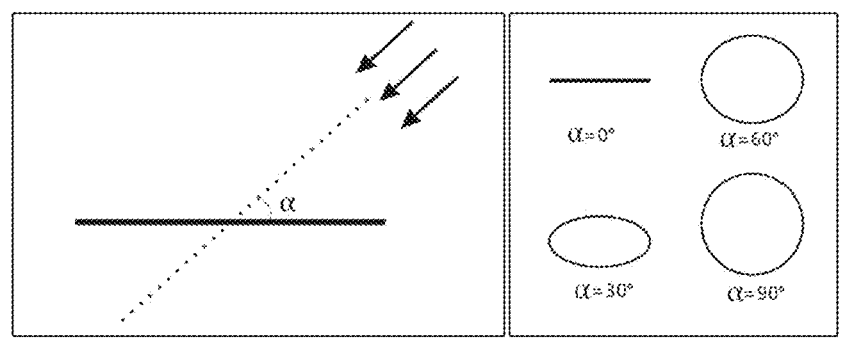
FIG. 6 is a schematic diagram of a shooting angle corresponding to a shooting shape in an embodiment of the method for determining rock wettability based on contact angle measurement and correction of multiple oil globules according to the present disclosure.

When the rock sample is cylindrical and its measurement surface is circular, the measurement surface of the rock sample can be directly taken as the shooting angle calibration circle. When the rock sample is irregular and its measurement surface is also irregular, it is necessary to place a shooting angle calibration circle on the measurement surface. FIG. 6 is a schematic diagram of a shooting angle corresponding to a shooting shape in an embodiment of the method for determining rock wettability based on contact angle measurement and correction of multiple oil globules according to the present disclosure. When the shooting angle $\alpha$ is 0°, the shooting shape is a straight line. When the shooting angle $\alpha$ is 0°-90°, the shooting shape is an ellipse. As the angle increases, the major axis of the ellipse remains unchanged, while the minor axis of the ellipse increases (the ellipse can be compared with those at $\alpha$=30° and at $\alpha$=60°). When the shooting angle $\alpha$ is 90°, the shooting shape is a circle.

S20. The image of the measurement surface of the rock sample with multiple oil globules at any shooting angle $\alpha$ and a deformation degree of the calibration circle in a shooting field of view are acquired, and the shooting angle $\alpha$ is calculated.

The shooting angle $\alpha$ is expressed in Eq. (1).

$$\alpha = \arcsin\left(\frac{S}{L}\right) \quad (1)$$

S denotes a length of a minor axis of a deformed ellipse of the calibration circle in the shooting field of view; L denotes a length of a major axis of the deformed ellipse of the calibration circle in the shooting field of view; and arcsin denotes an arcsine function.

The calibration using a circle as the shooting angle is only a preferred option. In other application scenarios, shapes such as square and checkerboard can also be selected for calibration, but the calculation of the shooting angle needs to be adjusted accordingly. The specific process will not be described in detail herein.

S30. Based on the shooting angle $\alpha$, contact angle measurement value $\gamma$ is corrected through a contact angle correction model to acquire contact angle correction value $\theta$.

The contact angle correction model is built as follows:

A10. A current shooting angle is set as a; and by taking any oil globule as a part of a sphere for sphere fitting, a physical model of the oil globule and the measurement surface of the rock sample is built based on an interfacial tension.

A20. A contact surface between the oil globule and the measurement surface of the rock sample in the physical model is set as plane BKCL; a center of a circle formed by the plane BKCL is set as point J; a shooting plane is set as plane GKHL; a center of a circle formed by the plane GKHL is set as point I, and a radius of the circle is set as r; a center of a fitted sphere is set as point O and a radius of the fitted sphere is set as R; a distance between the point I and the point J is set as line segment IJ, a distance between the point O and the point J is set as line segment OJ, and a distance between the point O and the point I is set as line segment OI; a supplementary angle of the contact angle measurement value $\gamma$ is set as angle $\beta$ and a supplementary angle of the contact angle correction value $\theta$ is set as angle $\beta$; and a mapping relation between the distance and the angle in the physical model is derived based on a side-angle relation of a right triangle.

The mapping relation between the distance and the angle in the physical model includes: a mapping relation from the line segment IJ to the radius r and the angle $\beta$; a mapping relation from the line segment IJ to the line segment OJ and the shooting angle $\alpha$; a mapping relation from the line segment OJ to the radius R and the angle $\beta$; a mapping relation from the line segment OI to the line segment OJ and the shooting angle $\alpha$; a triangle relation of the radius R, the radius r, and the line segment OI; a supplementary relation between the angle $\beta$ and the contact angle measurement value $\gamma$; and a supplementary relation between the angle $\varphi$ and the contact angle correction value $\theta$.

The mapping relation from the line segment IJ to the radius r and the angle $\beta$ is expressed in Eq. (2).

$$IJ = r \cos \beta \quad (2)$$

The mapping relation from the line segment IJ to the line segment OJ and the shooting angle $\alpha$ is expressed in Eq. (3).

$$IJ = OJ \cos \alpha \quad (3)$$

The mapping relation from the line segment OJ to the radius R and the angle $\varphi$ is expressed in Eq. (4).

$$OJ = R \cos \varphi \quad (4)$$

cos denotes a cosine function.

The mapping relation from the line segment OI to the line segment OJ and the shooting angle $\alpha$ is expressed in Eq. (5).

$$OI = OJ \sin \alpha \quad (5)$$

sin denotes a sine function.

The triangle relation of the radius R, the radius r, and the line segment OI, the supplementary relation between the angle $\beta$ and the contact angle measurement value $\gamma$, and the supplementary relation between the angle $\gamma$ and the contact angle correction value $\theta$ are expressed in Eq. (6) to Eq. (8), respectively.

$$OI^2 + r^2 = R^2 \quad (6)$$

$$\gamma = 180 - \beta \quad (7)$$

$$\theta = 180 - \varphi \quad (8)$$

A30. The mapping relation between the distance and the angle in the physical model are converted and solved to acquire a mapping relation from the contact angle correction value $\theta$ to the shooting angle $\alpha$ and the contact angle measurement value $\gamma$ as the contact angle correction model.

According to Eq. (2) to Eq. (8), the mapping relation from the contact angle correction value $\theta$ to the shooting angle $\alpha$ and the contact angle measurement value $\gamma$ is derived, as shown in Eq. (9).

$$\theta = \arccos\left(\frac{\cos\gamma}{\sqrt{\sin^2\alpha\cos^2\gamma + \cos^2\alpha}}\right) \quad (9)$$

arccos denotes an arccosine function, cos denotes a cosine function, and sin denotes a sine function.

The mapping relation shown in Eq. (9) is taken as the contact angle correction model. After the shooting angle $\alpha$ and the contact angle measurement value $\gamma$ are acquired, they are directly substituted into the model to acquire the contact angle correction value $\theta$. The method has high calculation efficiency and accuracy.

S40. Based on the contact angle correction value $\theta$, the wettability of the rock sample is determined.

The measurement of wettability does not simply divide the rock wettability into water wettability, oil wettability, and other types, but it can be comprehensively analyzed using the frequency distribution curve of the contact angle. The maximum, minimum, weighted average, and peak frequency of the contact angle can all be taken as parameters for quantitative characterization.

Figure 7:
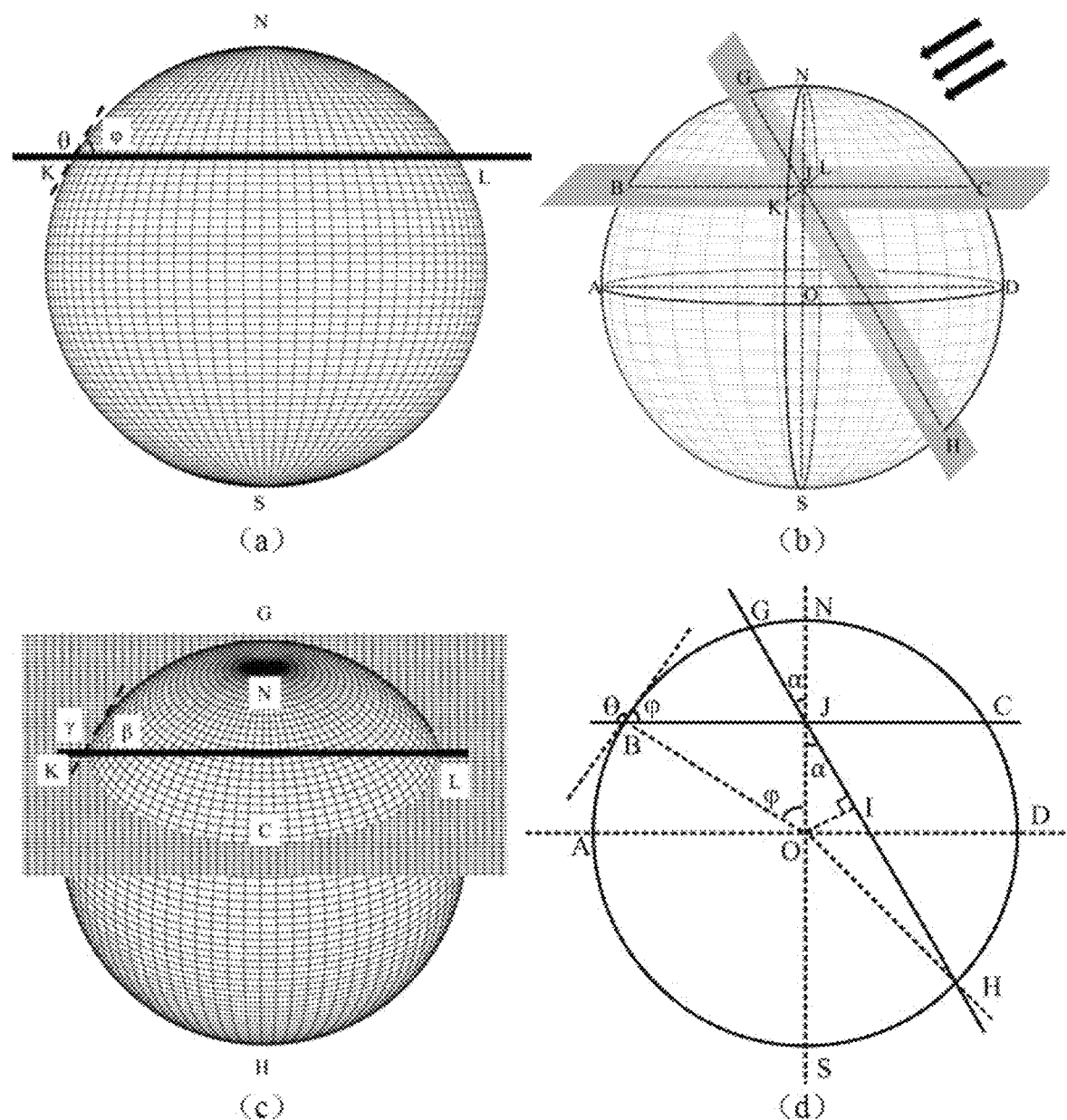
FIG. 7 is a schematic diagram of a mapping relation from a contact angle correction value θ to a contact angle measurement value γ and a shooting angle α in an embodiment of the method for determining rock wettability based on contact angle measurement and correction of multiple oil globules according to the present disclosure.

FIG. 7 is a schematic diagram of a mapping relation from the contact angle correction value θ to the contact angle measurement value γ and the shooting angle α in an embodiment of the method for determining rock wettability based on contact angle measurement and correction of multiple oil globules according to the present disclosure. In FIG. 7(a), the oil globule (spontaneous water imbibition and oil displacement) on the rock sample is considered as part of a sphere. From a horizontal perspective, KL denotes a test plane, and point N is the highest point of the oil globule. At the three-phase interface, the tangent angle between the oil globule and the rock surface is φ, and the contact angle θ is the angle between the water phase and the rock surface. The relation between the tangent angle and contact angle is shown in Eq. (8).

In FIG. 7(b), the shooting direction is at a certain angle to the measurement surface of the rock sample. On the three-dimensional schematic diagram, plane BCKL denotes the measurement surface of the rock sample, and plane GHKL denotes the contour surface actually photographed by the camera. On the plane BCKL, at the three-phase interface, the tangent angle of the liquid is the same. Therefore, the tangent angle at point K can be replaced by the tangent angle at point B. The angle between the plane GHKL and plane NSO is the shooting angle α, and the two planes intersect at line segment KL.

In FIG. 7(c), the camera captured the contour surface of the oil globule, including a portion of a circle denoted by curve KGL and a portion of an ellipse denoted by curve KCL. G is the highest point of the image, and it connects KL to form circular arc KGL. The tangent angle of the circular arc KGL at the point K is β, and its supplementary angle γ is the contact angle measurement value. The relation between the tangent angle and the supplementary angle is shown in Eq. (7).

FIG. 7(d) shows the geometric relations of the parameters. The tangent angle at the point B is φ, the angle between line segment GH and NS is a, and the radius of the large circle is R. Based on this, Eq. (4) is acquired.

According to FIG. 7(b), FIG. 7(c), and FIG. 7(d), the plane GHKL is a circular plane with a radius of r, a center of I, and a tangent angle of p at the point K. Based on this, Eq. (2) is acquired. Based on triangle OIJ, Eq. (3) and Eq. (5) are acquired. Based on triangle OHI, Eq. (6), Eq. (7) expressing the supplementary relation between the angle β and the contact angle measurement value γ, and Eq. (8) expressing the supplementary relation between the angle γ and the contact angle correction value θ are acquired. Finally, according to Eq. (2) to Eq. (8), the mapping relation from the contact angle correction value θ to the shooting angle α and the contact angle measurement value γ is acquired, as shown in Eq. (9).

The shooting angle α is defined as α∈[0°, 90°], and accordingly, the contact angle measurement value γ is defined as γ∈[0°, 180°].

Figure 8:
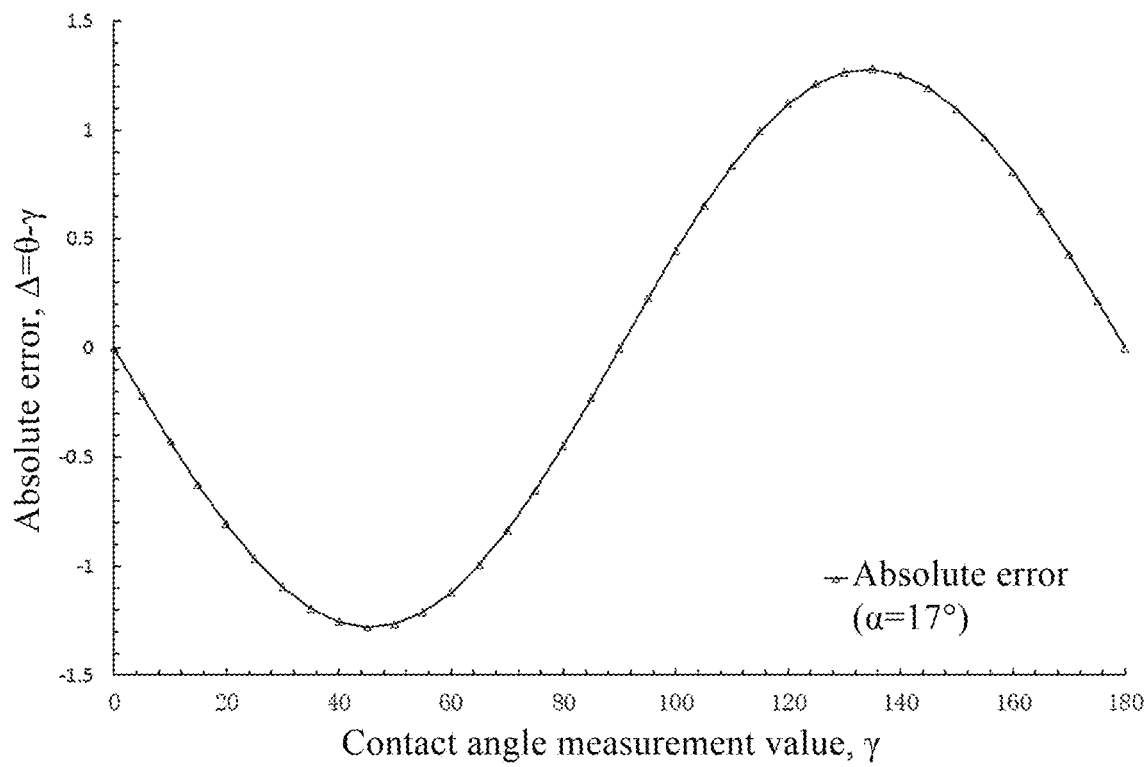
FIG. 8 is an error chart of the contact angle measurement value and the contact angle correction value in an embodiment of the method for determining rock wettability based on contact angle measurement and correction of multiple oil globules according to the present disclosure.

The spontaneous water imbibition and oil displacement on the rock sample shown in FIG. 4 is taken as an example for calculation. Firstly, according to the pixel values of the minor axis and the major axis, the shooting angle is calculated as α=17° according to Eq. (1). Then, an error chart of the contact angle measurement value and contact angle correction value is established according to Eq. (9), as shown in FIG. 8. The absolute errors corresponding to different contact angle measurement values are different, and it is necessary to correct the contact angle measurement values one by one to acquire the distribution map of the contact angle correction values. The frequency map of the contact angle correction values is shown in FIG. 9.

It is important to note that here, instead of correcting the distribution map of the contact angle measurement values, the contact angle measurement values are first corrected to form the frequency map of the contact angle correction values.

Figure 9:
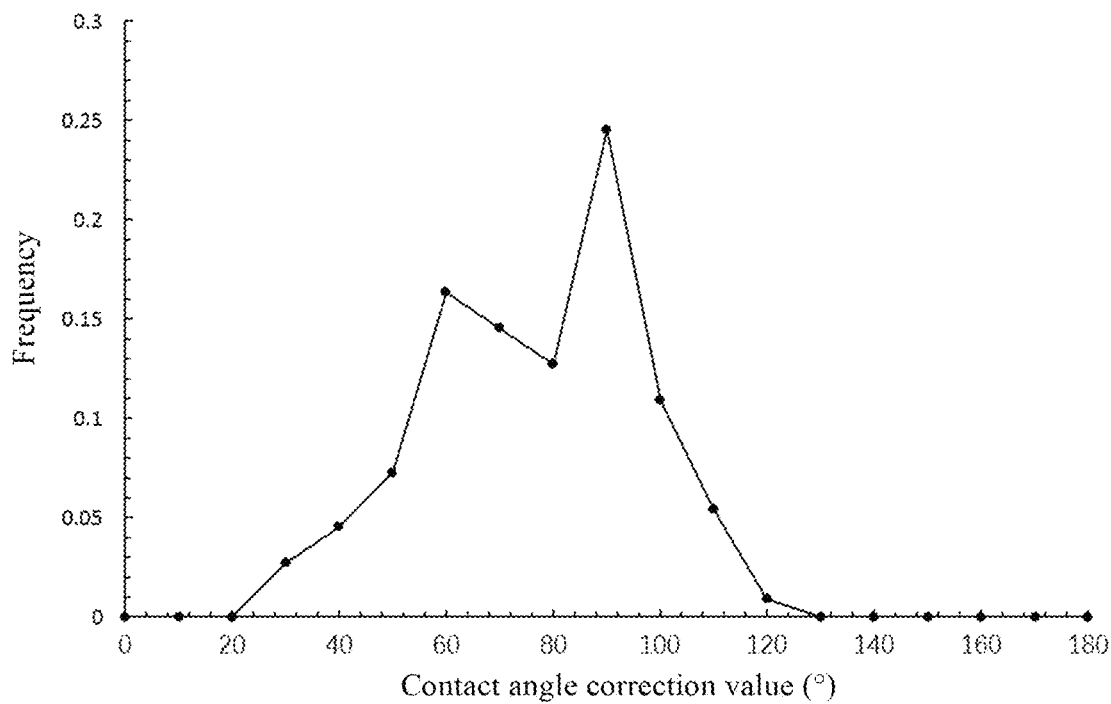
FIG. 9 is a frequency map of contact angle correction values in an embodiment of the method for determining rock wettability based on contact angle measurement and correction of multiple oil globules according to the present disclosure.

It is almost difficult to see the difference in the distribution maps shown in FIG. 5 and FIG. 9 with the naked eye. This is because the shooting angle of the camera is small (α=17°), resulting in a small error between the contact angle measurement value and the contact angle correction value, and also the statistical interval of the contact angle distribution map is relatively large. When the shooting angle of the camera increases and the statistical interval decreases, there will be a significant difference.

Figure 10:
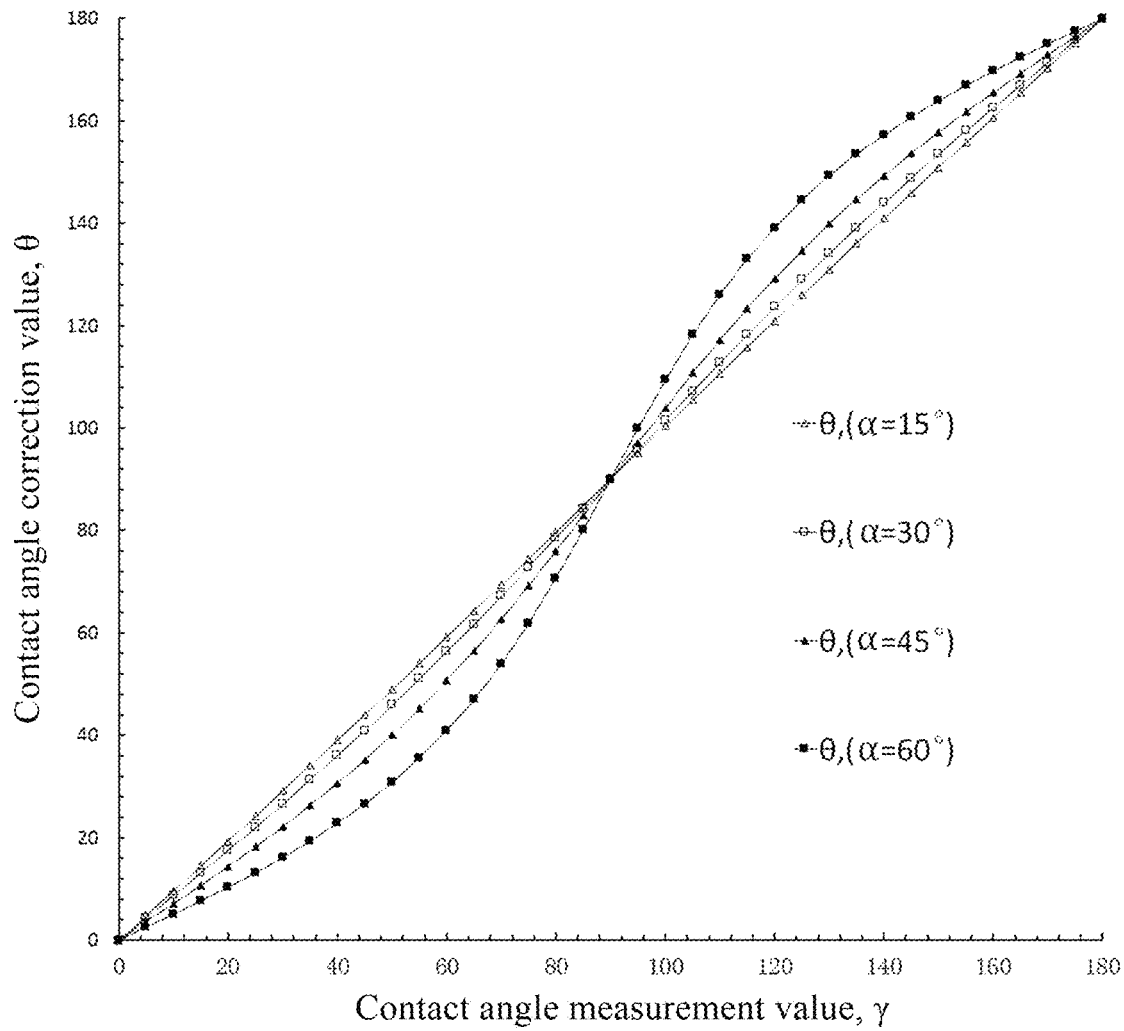
FIG. 10 shows a correspondence between the contact angle measurement value and the contact angle correction value at different shooting angles α=15°, 30°, 45°, 60° in an embodiment of the method for determining rock wettability based on contact angle measurement and correction of multiple oil globules according to the present disclosure.
Figure 11:
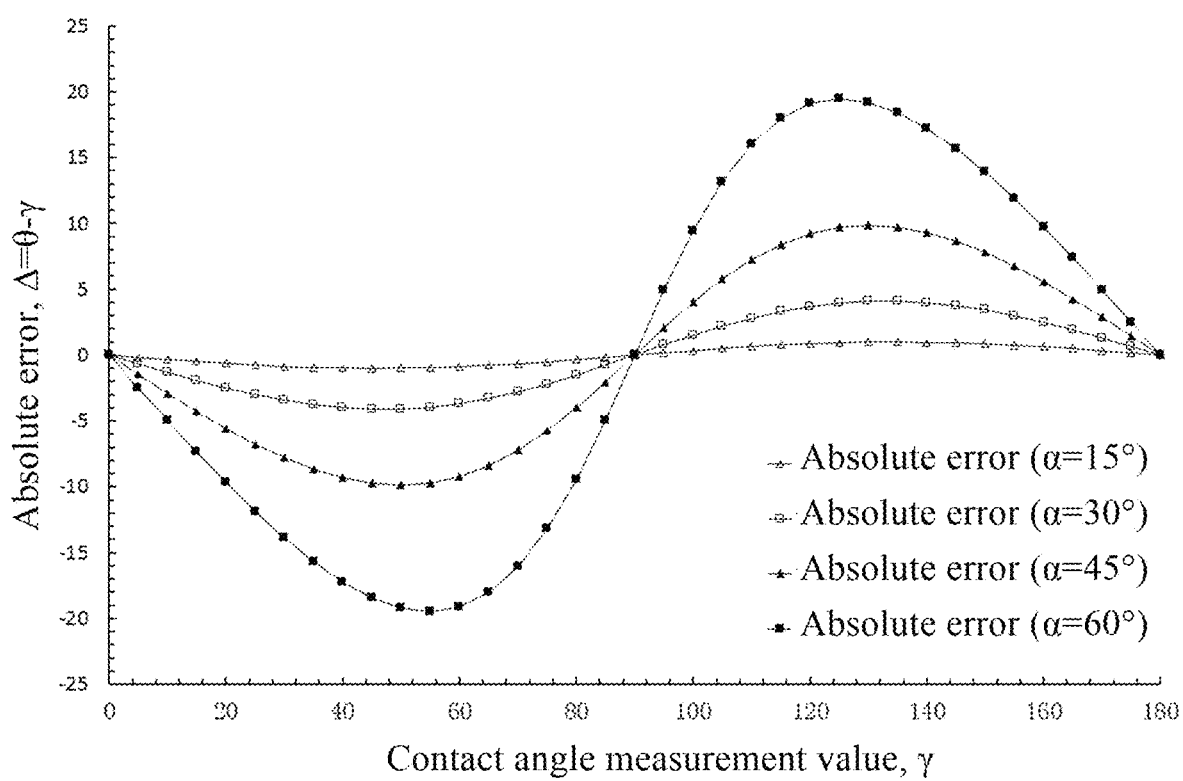
FIG. 11 shows an error chart of the contact angle measurement value and the contact angle correction value at different shooting angles α=15°, 30°, 45°, 60° in an embodiment of the method for determining rock wettability based on contact angle measurement and correction of multiple oil globules according to the present disclosure.

FIG. 10 and FIG. 11 respectively show a correspondence between the contact angle measurement value and the contact angle correction value and an error chart of the contact angle measurement value and the contact angle correction value at different shooting angles α=15°, 30°, 45°, 60° in an embodiment of the method for determining rock wettability based on contact angle measurement and correction of multiple oil globules according to the present disclosure. It can be seen that the error between the contact angle measurement value γ and the contact angle correction value θ varies. When the shooting angle α increases, the error between the contact angle measurement value and the contact angle correction value becomes increasingly large. Therefore, it is necessary to correct each contact angle measurement value based on different shooting angles and different contact angle measurement ranges so as to ensure the accuracy of the measurement results.

The error chart is configured to compare the error changes between the contact angle measurement value γ and the contact angle correction value θ at different shooting angles. In practical operation, after the shooting angle α and the contact angle measurement value γ are acquired, the contact angle correction value θ can be acquired based on the mapping relation from the contact angle correction value θ to the shooting angle α and the contact angle measurement value γ (i.e. based on the contact angle correction model). The calculation of the contact angle correction value does not need the error chart.

These steps are described in order in the above embodiments. However, those skilled in the art may understand that, in order to achieve the effects of these embodiments, different steps may not be necessarily executed in such an order, but may be executed simultaneously (in parallel) or in a reversed order. These simple changes should fall within the protection scope of the present disclosure.

A third embodiment of the present disclosure provides a system for determining rock wettability based on contact angle measurement and correction of multiple oil globules, which includes: a rock sample preparation module, a shooting angle acquisition module, a contact angle correction module, and a wettability determination module.

The rock sample preparation module is configured to saturate a rock sample with oil, place a shooting angle calibration circle on a measurement surface of the rock sample, and place the rock sample saturated with oil in water for a set time to form a rock sample with multiple oil globules.

The shooting angle acquisition module is configured to acquire an image of the measurement surface of the rock sample with multiple oil globules at any shooting angle α and a deformation degree of the calibration circle in a shooting field of view, and calculate the shooting angle α.

The contact angle correction module is configured to correct, based on the shooting angle α, a contact angle measurement value γ through a contact angle correction model to acquire a contact angle correction value θ.

The wettability determination module is configured to determine, based on the contact angle correction value θ, the wettability of the rock sample.

Those skilled in the art should clearly understand that, for convenience and brevity of description, reference is made to corresponding processes in the above method embodiments for specific working processes and related description of the system, and details are not described herein again.

It should be noted that the system for determining rock wettability based on contact angle measurement and correction of multiple oil globules provided by the above embodiments is only described by taking the division of the above functional modules as an example. In practical applications, the above functions can be completed by different functional modules as required, that is, the modules or steps in the embodiments of the present disclosure are further decomposed or combined. For example, the modules of the above embodiments may be combined into one module, or may be further divided into multiple sub-modules to complete all or part of the functions described above. The names of the modules and steps involved in the embodiments of the present disclosure are only for distinguishing each module or step, and should not be regarded as improper limitations on the present disclosure.

A fourth embodiment of the present disclosure provides an electronic device. The electronic device includes:

at least one processor; and a memory in communication connection with the at least one processor, where the memory stores an instruction executable by the processor, and the instruction is executed by the processor to implement the above method for determining rock wettability based on contact angle measurement and correction of multiple oil globules.

A fifth embodiment of the present disclosure proposes a computer-readable storage medium. The computer-readable storage medium stores a computer instruction, and the computer instruction is executed by a computer to implement the above method for determining rock wettability based on contact angle measurement and correction of multiple oil globules.

Those skilled in the art should clearly understand that, for convenience and brevity of description, reference is made to corresponding processes in the above method embodiments for specific working processes and related description of the storage device and processing device, and details are not described herein again.

Those skilled in the art should be aware that the modules and method steps of the examples described in the embodiments disclosed herein may be implemented by electronic hardware, computer software, or a combination thereof. The programs corresponding to software modules and method steps may be placed in random access memory (RAM), internal memory, read-only memory (ROM), electrically programmable ROM, electrically erasable programmable ROM, registers, hard disk, removable disk, compact disc read-only memory (CD-ROM), or in any other form of storage medium known in the technical field. In order to clearly illustrate the interchangeability of the electronic hardware and software, the composition and steps of each example are generally described in accordance with the function in the above description. Whether the functions are performed by electronic hardware or software depends on particular applications and design constraints of the technical solutions. Those skilled in the art may use different methods to implement the described functions for each specific application, but such implementation should not be considered to be beyond the scope of the present disclosure.

Terms such as "first" and "second" are intended to distinguish between similar objects, rather than describe or indicate a specific order or sequence.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present disclosure are described with reference to the preferred implementations and drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions after these changes or substitutions should fall within the protection scope of the present disclosure.

What is claimed is:

1. A system for determining rock wettability based on contact angle measurement and correction of multiple oil globules, comprising a first treatment tank, a second treatment tank, a mechanical arm, an image acquisition device, and a control processor, wherein the first treatment tank is an oil tank and the second treatment tank is a water tank; and the oil tank and the water tank are arranged in an operation zone of the mechanical arm;

the mechanical arm is configured to receive a first control signal and a second control signal from the control processor;

the mechanical arm is further configured to grab a target rock sample based on the first control signal, place the target rock sample in the first treatment tank, and maintain the target rock sample for a set first time to saturate the target rock sample with oil;

the mechanical arm is further configured to place the target rock sample saturated with oil in the second treatment tank based on the second control signal, and maintain the target rock sample for a set second time for water imbibition and oil displacement, such that oil globules appear on a measurement surface of the target rock sample to form a rock sample with the oil globules, wherein a measurement surface of the rock sample with the oil globules is provided with a shooting angle calibration circle;

the image acquisition device is configured to receive an image acquisition control signal from the control processor and photograph the measurement surface of the rock sample with the oil globules at a shooting angle α; and the control processor is configured to generate the first control signal, the second control signal, and the image acquisition control signal, and control the mechanical arm and the image acquisition device separately; and the control processor is further configured to determine, based on an image of the measurement surface of the rock sample with the oil globules acquired by the image acquisition device at the shooting angle α, wettability of the rock sample by a method for determining rock wettability based on contact angle measurement and correction of the oil globules.

2. A method for determining rock wettability based on contact angle measurement and correction of multiple oil globules, based on the system according to claim 1, and comprising:

S10: saturating the rock sample with oil, placing the shooting angle calibration circle on the measurement surface of the rock sample and placing the rock sample saturated with oil in water for a set time to form the rock sample with the oil globules;

S20: acquiring the image of the measurement surface of the rock sample with the oil globules at the shooting angle α and a deformation degree of the shooting angle calibration circle in a shooting field of view, and calculating the shooting angle α;

S30: correcting, based on the shooting angle α, a contact angle measurement value γ through a contact angle correction model to acquire a contact angle correction value θ; and S40: determining, based on the contact angle correction value θ, the wettability of the rock sample.

3. The method according to claim 2, wherein the shooting angle α is expressed as:

$$\alpha = \arcsin\left(\frac{S}{L}\right)$$

wherein, S denotes a length of a minor axis of a deformed ellipse of the shooting angle calibration circle in the shooting field of view; L denotes a length of a major axis of the deformed ellipse of the shooting angle calibration circle in the shooting field of view; and arcsin denotes an arcsine function.

4. The method according to claim 2, wherein the contact angle correction model is established as follows:

A10: setting a current shooting angle as a; and establishing, by taking an oil globule as a part of a sphere for sphere fitting, a physical model of the oil globule and the measurement surface of the rock sample based on an interfacial tension;

A20: setting a contact surface between the oil globule and the measurement surface of the rock sample in the physical model as a plane BKCL; setting a center of a circle formed by the plane BKCL as a point J; setting a shooting plane as a plane GKHL; setting a center of a circle formed by the plane GKHL as a point I and a radius of the circle as r; setting a center of a fitted sphere as a point O and a radius of the fitted sphere as R; setting a distance between the point I and the point J as a line segment IJ, a distance between the point O and the point J as a line segment OJ, and a distance between the point O and the point I as a line segment OI; setting a supplementary angle of the contact angle measurement value γ as an angle β and a supplementary angle of the contact angle correction value θ as an angle γ; and deriving a mapping relation between the distance and the angle in the physical model based on a side-angle relation of a right triangle;

wherein, the mapping relation between the distance and the angle in the physical model comprises: a mapping relation from the line segment IJ to the radius r and the angle β; a mapping relation from the line segment IJ to the line segment OJ and the current shooting angle α; a mapping relation from the line segment OJ to the radius R and the angle φ; a mapping relation from the line segment OI to the line segment OJ and the current shooting angle α; a triangle relation of the radius R, the radius r, and the line segment OI; a supplementary relation between the angle β and the contact angle measurement value γ; and a supplementary relation between the angle φ and the contact angle correction value θ; and A30: converting and solving the mapping relation between the distance and the angle in the physical model to acquire a mapping relation from the contact angle correction value θ to the current shooting angle α and the contact angle measurement value γ as the contact angle correction model.

5. The method according to claim 4, wherein the mapping relation from the line segment IJ to the radius r and the angle β is expressed as follows:

$$IJ = r \cos \beta$$

wherein, cos denotes a cosine function.

6. The method according to claim 4, wherein the mapping relation from the line segment IJ to the line segment OJ and the current shooting angle α is expressed as follows:

$$IJ = OJ \cos \alpha$$

wherein, cos denotes a cosine function.

7. The method according to claim 4, wherein the mapping relation from the line segment OJ to the radius R and the angle φ is expressed as follows:

$$OJ = R \cos \varphi$$

wherein, cos denotes a cosine function.

8. The method according to claim 4, wherein the mapping relation from the line segment OI to the line segment OJ and the current shooting angle α is expressed as follows:

$$OI = OJ \sin \alpha$$

wherein, sin denotes a sine function.

9. The method according to claim 4, wherein the triangle relation of the radius R, the radius r, and the line segment OI, the supplementary relation between the angle β and the contact angle measurement value γ, and the supplementary relation between the angle φ and the contact angle correction value θ are expressed as follows:

$$OI^2 + r^2 = R^2$$

$$\gamma = 180 - \beta$$

$$\theta = 180 - \varphi.$$

10. The method according to claim 4, wherein the contact angle correction value θ is expressed as:

$$\theta = \arccos\left(\frac{\cos\gamma}{\sqrt{\sin^2\alpha\cos^2\gamma + \cos^2\alpha}}\right)$$

wherein, arccos denotes an arccosine function, cos denotes a cosine function, and sin denotes a sine function.

* * * * *